July 28, 1964 B. R. Z. BRUNNEN Plant Pat. 2,429

STRAWBERRY PLANT

Filed Nov. 15, 1962

INVENTOR
BERTHA ROSA ZUM BRUNNEN
BY Williamson & Palmatier
ATTORNEYS

United States Patent Office

Plant Pat. 2,429
Patented July 28, 1964

2,429
STRAWBERRY PLANT

Bertha Rosa Zum Brunnen, Rte. 1, Clearwater, Minn.
Filed Nov. 15, 1962, Ser. No. 238,068
1 Claim. (Cl. Plt.—49)

Figure 2:
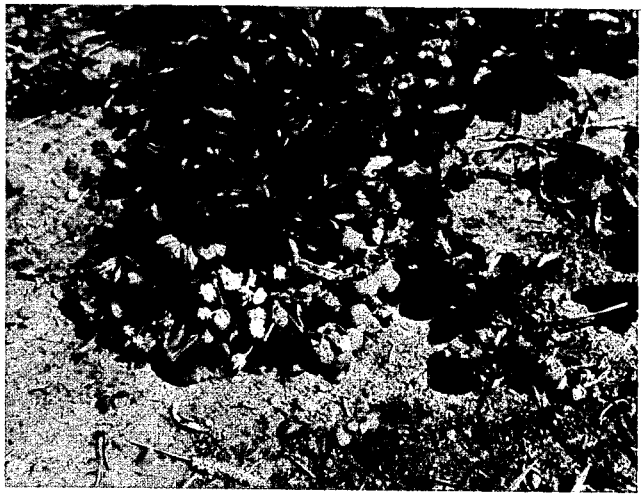

My invention and discovery relates to a new and distinct variety of everbearing strawberry plant which is seedling discovered and selected by me from plants produced from a large number of seeds which I selected and planted in a cultivated area of my nursery near Clearwater, Minnesota. From the original mother plant discovered in my cultivated fields, I have asexually reproduced a very large number of distinctive plants of this new variety by transplanting rooted runner plants therefrom.

An object of my invention has been to produce a new variety of strawberry plant of the everbearing type, having greater uniformity of fruit, great productivity throughout the entire growing season and having a new distinctive taste and chewing texture, as contrasted, with the well known and outstanding everbearing varieties.

A further object has been to produce such a new distinctive variety of strawberry plant where the fruit or berries therefrom are substantially uniform in shape and color when fully grown, and will continue of such size and shape throughout the entire growing season, and where the taste thereof is truly distinguished as contrasted with all other everbearing strawberries known by me, being less acid than such well known plants as the "Gem" strawberry and the "Wayzata" strawberry, but having a rich, distinctive and somewhat tangy taste as distinguished from strawberries which are blandly sweet.

My new, distinctive variety of everbearing strawberry plant may be generally characterized by its great hardiness, fruit productivity, its uniformity of a truly heart-shaped berry and its unusually rich, tangy taste, without leaving an aftertaste of acidity, as well as the rather fine chewing texture, as contrasted with well known everbearing strawberries, including "Gem," "Red Rich," "Honey Lump," "Wayzata" and "Ogallala."

Careful observation of my new variety has shown that the plants and leaves have good resistance to "leaf spot" (caused by insects) and "leaf roller," such resistance in my experience, being better than the "Gem," "Red Rich" and the "Brilliant" variety disclosed in Plant Patent No. 1,183.

My new strawberry plants have medium-heavy crowns and have a medium number of heavy runners which root and quickly grow into plants. Many of said runner plants start bearing during the first season.

The prime berries of both mother plant and runner plants are quite uniformly colored an intense, medium dark red and are quite glossy. The flesh of the berries is firm, juicy and has a more delicate chewing texture than many of the presently well known everbearing strawberries. The flesh of the berries, as shown upon longitudinal or axial slicing, has a relatively thick stratum of red flesh extending further inwardly from the periphery than in most everbearing berries and almost universally in my variety, a relatively narrow, white outline is defined centrally of the berry, in cross-sectional shape of a spinning top. The central, axial flesh of the berry within the white outline is firm, with substantially no voids or inner core.

Figure 1:
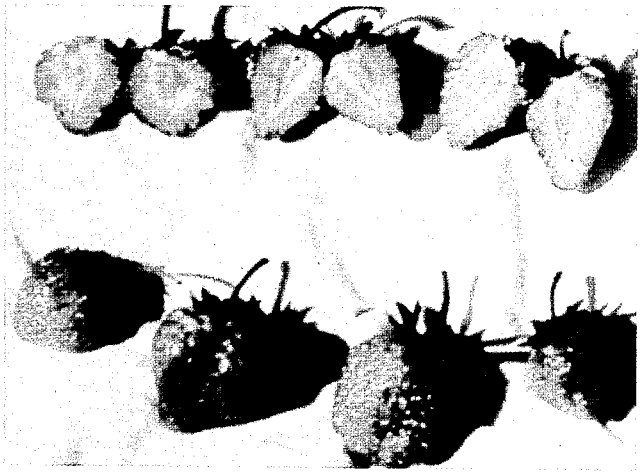

In the accompanying drawings, several typical berries as well as blossoms and entire plants, are illustrated in color. In said drawings:

FIG. 1 is a perspective colored view showing several typical berries externally, in prime condition, together with several berries which have been axially or stem-sliced to show the interiors of the flesh; and FIG. 2 is a perspective colored view showing a typical plant of my new variety growing in the soil, with berries in various stages of ripening thereon, and with blossoms and also showing runner plants, some with berries developed thereon.

To facilitate comparison of characteristics of my new plant with other well known varieties, the following summary and detailed description of my new variety is given, to wit:

*Plant Characteristics*

Growth: Hardy with many fruit stems, quite heavily leafed and characterized by rapid growth of new plants from runners, throughout the growing season.

Size of roots: Medium thick, finer roots than in the "Gem" or "Red Rich."

Crown size: Larger than "Gem" and "Red Rich"—about the size of the crowns in U.S. Plant Patent 1,989, "Honey Lump."

Leaves: Almost always trifoliate, darker green than those of the "Gem" and "Red Rich"; darker than the plant of Plant Patent No. 1,183, "Brilliant."

Petiole: Longer than "Gem" and "Red Rich"; intermediate shade of green with abundant pubescence, longer than "Ogallala."

Leaflets: Quite prolific, generally oval in shape with small ends of oval attached to stem; serrations distinctive and peculiar in that each has somewhat of an arrowhead shape as distinguished from the leaflets of such varieties as "Honey Lump" and "Red Rich," which have saw-tooth, peripheral serrations. Upper surfaces generally slightly darker than the plants of "Red Rich" and "Gem"; cupped more than doublet "Gem" and "Red Rich," and slightly darker than "Ogallala."

Runners: Fairly abundant; tendrils long, less thickness than patented "Honey Lump," and "Gem." Medium-pubescent.

Flower stems: Medium long, substantially longer than "Gem" and those of Patent 1,183. Flowers well shaped, rounded outer petal edges; centers lighter yellow than those of "Gem" and Patent 1,183 and "Red Rich," "Wayzata" and "Ogallala"; stamen rather uniform and short.

Sex: Bi-sexual.

Fruit stems: Medium heavy, long, somewhat heavier than "Red Rich," U.S. Plant Patent No. 993, characterized by frequency of small leaflets and stem; substantially longer than "Gem."

Soil: Grows best in moderately sandy loam.

Frost resistance: Excellent, very hardy in typical northern U.S. climates, having high humidity averages in the fall, in my experience more hardy than "Gem," "Ogallala" and "Red Rich" varieties, even in latitudes in the State of Minnesota, fifteen miles north of Brainerd.

Rain and moisture resistance: Excellent.

Drought resistance: Good.

*Fruit Characteristics*

Condition described in specification—prime. Prime berries obtained during entire growing season including many from runner plants that season. Quite uniformly colored externally, medium dark red.

Average growing size: Axial length from 1¼ to 1½ on prime berries; slightly larger and very different in shape than "Red Rich" and most "Ogallala" berries, about the size of "Gem" berries in volume, though different in shape. Characterized by an unusually full heart shape which is very noticeable when berries sliced longitudinally. The body of the berry is quite uniformly conically tapered to a pointed apex, the base where the stem is attached having a depressed portion which completes the heart shape of the berries. This heart shape is typical and characteristic of most all of the berries grown.

Surface and aspect: Glossy, prime berries uniformly colored throughout quite intensely, a medium dark red falling within the range illustrated in Maerz and Paul Dictionary of Color, 2nd edition, published by McGraw-Hill Book Company of New York City, and shown on Plate 5, page 33, color horizontal column 5, ranging from G to L on the intersecting vertical column.

Flesh: Substantially solid throughout, quite juicy with a relatively thick stratum of red flesh only very slightly lighter than the external color, extended further inwardly from the periphery than in most known berries, including "Red Rich, "Ogallala" Plant Patent 1,183; the "Gem," and "Honey Lump." The flesh contains a relatively thin, white area defining, when the berry is longitudinally sliced, a configuration of a spinning top in almost all berries. The chewing texture of the berries is excellent and relatively fine, as contrasted with coarser textured berries such as the "Gem," the berries of Plant Patent 1,183 and the "Red Rich" berry.

Seeds: Relatively smaller than the seeds of "Ogallala" "Red Rich," Plant Patent 993; patented "Honey Lump." Seeds protrude very slightly from berry periphery.

Fruit flavor: A distinctive and rather intensely rich flavor, brisk and mellow, differing substantially from the more bland taste of "Ogallala" berries; less acid than "Wayzata," "Gem" and Patent 1,183; nice after-taste with tanginess but without noticeable acidity.

Calyx: Supple tips curve outwardly and upwardly from the base of the berry, more so than in other varieties known to applicant.

Keeping qualities: Good shipping qualities; intense rich taste of berries, which characteristics enable unusual rich taste to be present in frozen berries; color well retained in canning or freezing.

My strawberry plant and the fruit produced thereby may vary in slight details depending upon whether conditions and the soil conditions in which they are raised, all within the scope of my invention.

What is claimed is:

A new and distinct variety of everbearing strawberry plant substantially as herein shown and described, characterized by the fruit of said plant being usually rounded heart shape, tapering to a blunt point, having a longitudinal axis somewhat greater than the maximum diameter and having a base indented at the point of connection with the berry stem to complete the heart shape, the flesh of the fruit being characterized by a firmness throughout and exhibiting when longitudinally or stem-cut, a relatively narrow outline simulating in configuration that of a spinning top with the flesh within said outline being for the most part of a similar color and depth to that of the flesh between said outline and the periphery, said plant being further characterized by production of hardy runner plants, many of which bear fully matured fruit the first season, the external aspects of the fruit being glossy and of an intense, medium dark red color within the range described herein, and taste of the prime berries being rather intense and rich but without noticeable acidity.

No references cited.